(12) United States Patent
De Araujo et al.

(10) Patent No.: US 11,944,177 B2
(45) Date of Patent: Apr. 2, 2024

(54) CONDITIONING AND STYLING REACTIVATED HAIR DEVICE

(71) Applicants: Igor De Araujo, Ft. Lauderdale, FL (US); Chad Alan Pendley, Ft. Lauderdale, FL (US)

(72) Inventors: Igor De Araujo, Ft. Lauderdale, FL (US); Chad Alan Pendley, Ft. Lauderdale, FL (US)

( * ) Notice: Subject to any disclaimer, the term of this patent is extended or adjusted under 35 U.S.C. 154(b) by 1129 days.

(21) Appl. No.: 16/513,553

(22) Filed: Jul. 16, 2019

(65) Prior Publication Data
US 2021/0015234 A1 Jan. 21, 2021

(51) Int. Cl.
| | |
|---|---|
| A45D 24/28 | (2006.01) |
| A45D 24/00 | (2006.01) |
| A45D 24/22 | (2006.01) |
| A46B 5/02 | (2006.01) |
| A46B 11/00 | (2006.01) |
| A46B 13/02 | (2006.01) |
| A61K 8/73 | (2006.01) |

(52) U.S. Cl.
CPC .............. *A45D 24/28* (2013.01); *A45D 24/00* (2013.01); *A45D 24/007* (2013.01); *A45D 24/22* (2013.01); *A46B 5/021* (2013.01); *A46B 11/0006* (2013.01); *A46B 11/0096* (2013.01); *A46B 13/023* (2013.01); *A61K 8/735* (2013.01); *A45D 2024/002* (2013.01); *A45D 2200/207* (2013.01); *A46B 2200/104* (2013.01)

(58) Field of Classification Search
CPC ...... A45D 24/28; A45D 24/007; A45D 24/10; A45D 24/22; A45D 2024/002; A45D 2200/207; A46B 13/02
See application file for complete search history.

(56) References Cited

U.S. PATENT DOCUMENTS 5,261,426 A * 11/1993 Kellett ................. A46B 11/001
424/70.13
5,622,192 A 4/1997 Chiou
(Continued)

FOREIGN PATENT DOCUMENTS

| CN | 108937064 | * 12/2018 | ............. A45D 24/10 |
| CN | 109315909 | *  2/2019 | ............. A45D 24/10 |

(Continued)

*Primary Examiner* — J C Jacyna

(57) ABSTRACT

A conditioning and styling reactivated hair device is an apparatus which can be used to spray formulations to condition, style, reactivate, and/or refresh hair, stimulate the scalp, and help detangle hair. The apparatus includes a handheld grip, a detachable panel, a nebulizing mechanism, a vibration mechanism, and a control system. The handheld grip serves as the base for the apparatus which can be ergonomically held by one hand. Further, the handheld grip includes a palm-bearing surface and an interfacing surface. The detachable panel covers the internal structure of the handheld grip and supports external hair styling aids. The detachable panel further comprises a back plate and a flow guide. The nebulizing mechanism dispenses spray formulations stored within the handheld grip. The vibration mechanism generates physical vibrations for stimulating purposes as well as to aid in dispensing spray formulations. The control system enables the semi-automatic operation of the apparatus by users.

19 Claims, 11 Drawing Sheets

(56) References Cited

U.S. PATENT DOCUMENTS

| | | | |
|---|---|---|---|
| 6,257,246 B1 | 7/2001 | Kan | |
| 6,283,930 B1 | 9/2001 | Purvis et al. | |
| 8,083,696 B2 | 12/2011 | Vandenbelt et al. | |
| 9,597,702 B1 * | 3/2017 | Ciervo | B05B 17/0676 |
| 10,172,324 B2 | 1/2019 | Lou | |
| 10,631,625 B1 * | 4/2020 | Alhajji | A45D 24/22 |
| 2008/0167590 A1 * | 7/2008 | Jon | A45D 34/042 |
| | | | 601/160 |
| 2013/0008388 A1 | 1/2013 | Chancy et al. | |
| 2014/0013607 A1 * | 1/2014 | Funayama | F26B 7/00 |
| | | | 34/60 |
| 2014/0209702 A1 * | 7/2014 | Weng | B05B 12/004 |
| | | | 239/74 |
| 2017/0027301 A1 * | 2/2017 | Mazed | A61M 35/003 |
| 2018/0028046 A1 * | 2/2018 | Macca | A46B 9/023 |
| 2018/0139928 A1 * | 5/2018 | Takla | A01K 13/001 |

FOREIGN PATENT DOCUMENTS

| | | | | |
|---|---|---|---|---|
| CN | 110200389 | * | 9/2019 | A45D 24/10 |
| WO | WO2001000057 A1 | | 1/2001 | |
| WO | WO2013051693 | * | 4/2013 | A45D 2200/207 |

* cited by examiner

34

Spray Formulations

Hyaluronic Acid

FIG. 11

CONDITIONING AND STYLING REACTIVATED HAIR DEVICE

FIELD OF THE INVENTION

The present invention relates generally to hair devices and hair conditioning appliances. More specifically, the present invention relates to a hair device which nebulizes liquids and solutions for the purpose of applying hair conditioning, styling, and/or reactivating with the purpose of reactivating previously existent products in the hair without wetting, greasing, or making the hair hard to the touch.

BACKGROUND OF THE INVENTION

An objective of the present invention is to provide a hair device that utilizes a nebulizing mechanism to store and nebulize waterless spray formulations. The waterless spray formulations can include specially made solutions for the purpose of applying hair conditioning, styling hair products, and/or hair treatments into the hair without wetting the hair, making the hair greasy, nor hard to the touch. No heat element is utilized so the spray formulations do not change properties. The spray formulations preferably use Hyaluronic acid as the main active ingredient. Another objective of the present invention is to provide an ergonomic conditioning and styling reactivated hair device which refreshes the hair. The present invention does not have a handle. Instead, the present invention provides an ergonomic design to fit comfortable on the closed palm of a hand.

Furthermore, the present invention provides a stimulation massage feature which can be used at the same time as the nebulizing mechanism. In some embodiments, the present invention provides a detachable brush cushion with different options of bristles to use on dry hair or wet hair. The detachable brush cushion enables proper sanitation of the bristles whether the bristles are beaded, thinner, and/or flexible for brushing through wet hair, or to be used with hair extensions. The present invention can also be utilized for detangling hair. Finally, the present invention provides an internal timer to shut off the nebulizing mechanism and massage feature after a certain time, with LED light indicators as well to help visually monitor the operation of the present invention.

BRIEF DESCRIPTION OF THE DRAWINGS

FIG. 11 is a schematic view of the spray formulations showing Hyaluronic acid as the main active ingredient of the spray formulations.

DETAIL DESCRIPTIONS OF THE INVENTION

All illustrations of the drawings are for the purpose of describing selected versions of the present invention and are not intended to limit the scope of the present invention.

Figure 1:
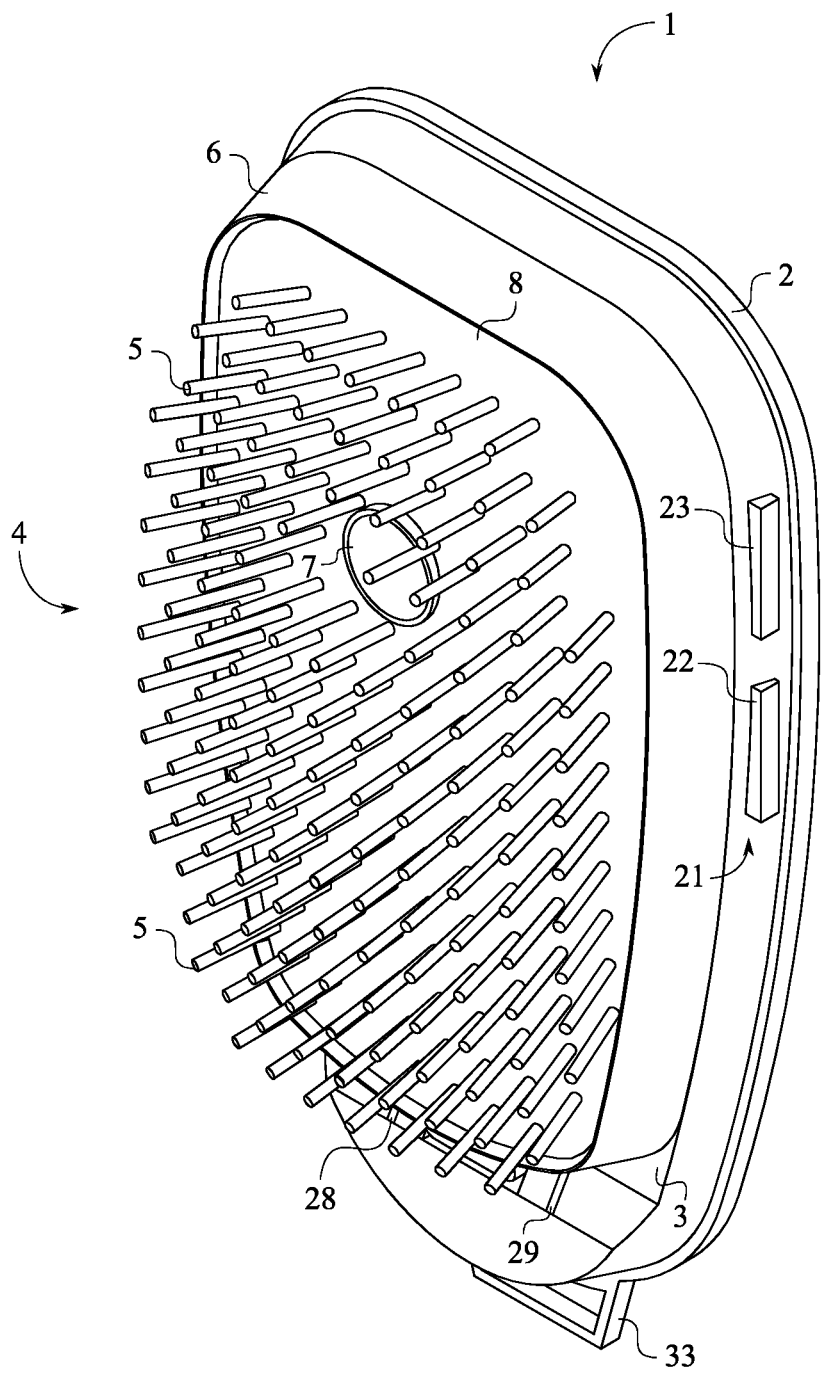
FIG. 1 is a top front perspective view showing the conditioning and styling reactivated hair device, wherein the detachable panel is shown attached to the handheld grip.
Figure 2:
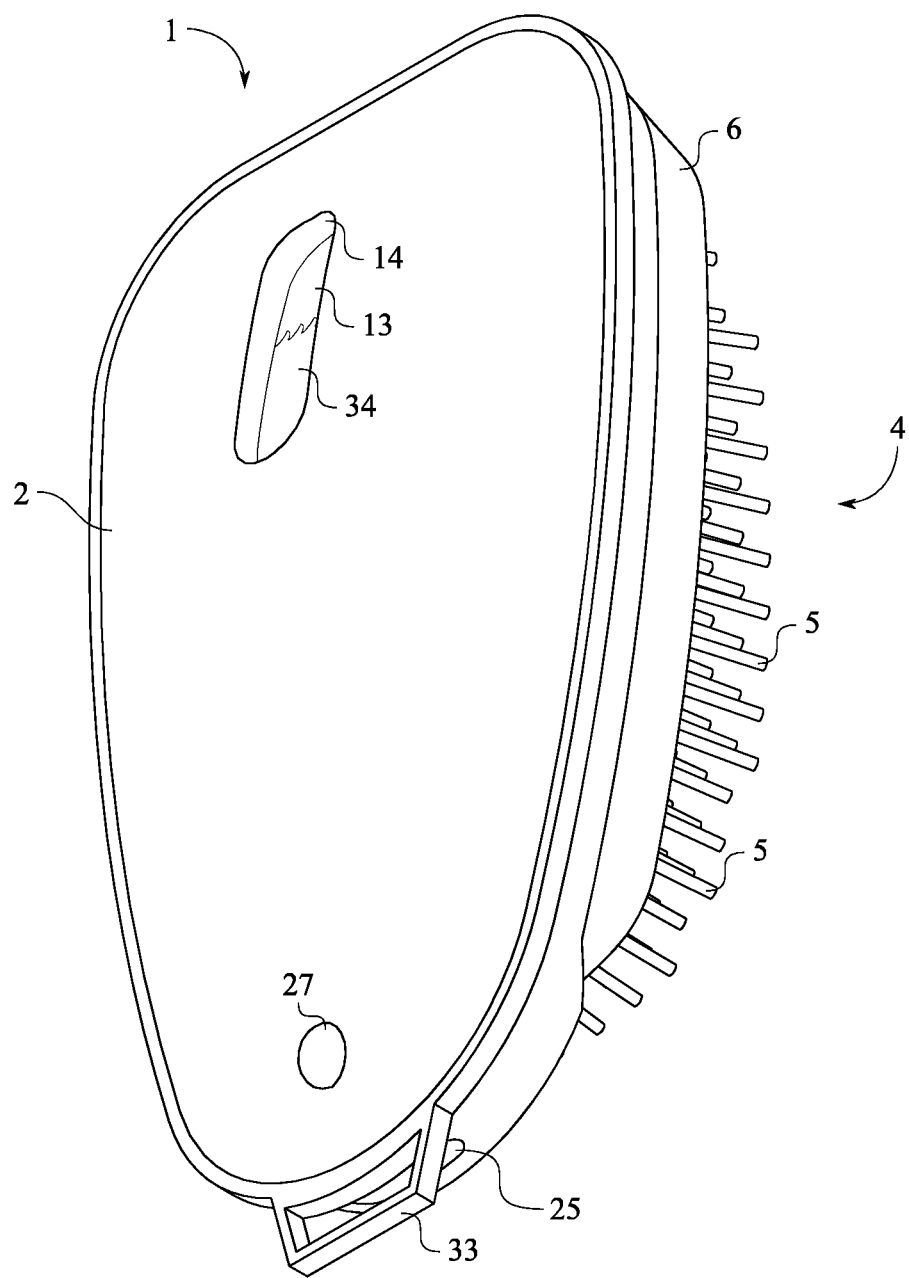
FIG. 2 is a bottom rear perspective view showing the conditioning and styling reactivated hair device, wherein the detachable panel is shown attached to the handheld grip.
Figure 7:
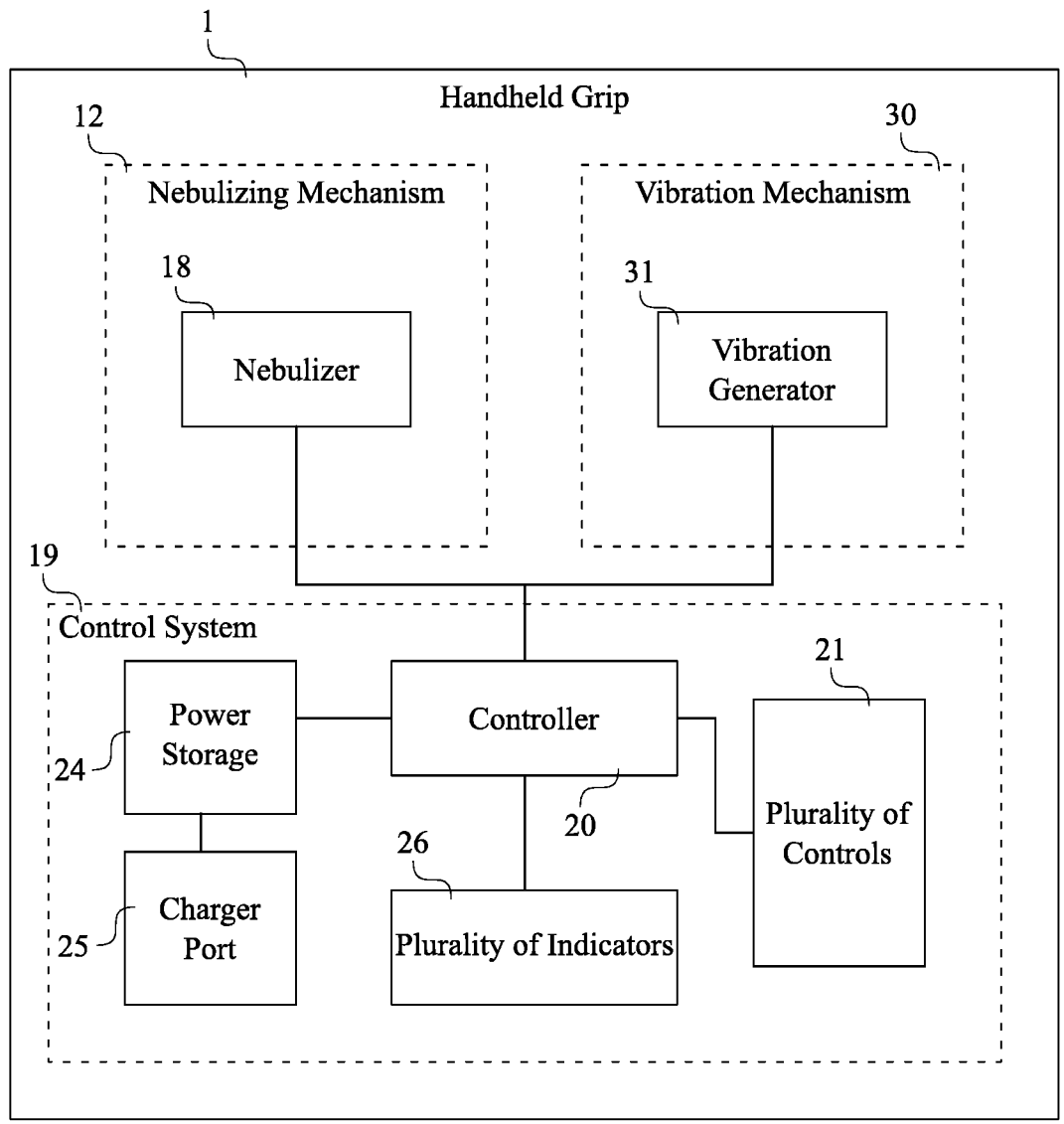
FIG. 7 is a schematic view of the conditioning and styling reactivated hair device showing the control system electronically connected to the nebulizing mechanism and the vibration mechanism within the handheld grip.

The present invention is a conditioning and styling reactivated hair device which can be used to spray formulations to condition/style hair, restyle and stimulate the scalp, and help detangle hair. As can be seen in FIGS. 1, 2, and 7, in a preferred embodiment, the present invention comprises a handheld grip 1, a detachable panel 4, a nebulizing mechanism 12, a vibration mechanism 30, and a control system 19. The handheld grip 1 serves as the base for the present invention which can be ergonomically held by one hand. The detachable panel 4 covers the internal structure of the handheld grip 1 and can also support external hair styling aids. The nebulizing mechanism 12 dispenses spray formulations 34 stored within the handheld grip 1. The vibration mechanism 30 generates physical vibrations for stimulating purposes as well as to aid in the dispensing of spray formulations 34. Finally, the control system 19 enables the semi-automatic operation of the present invention by the users.

Figure 3:
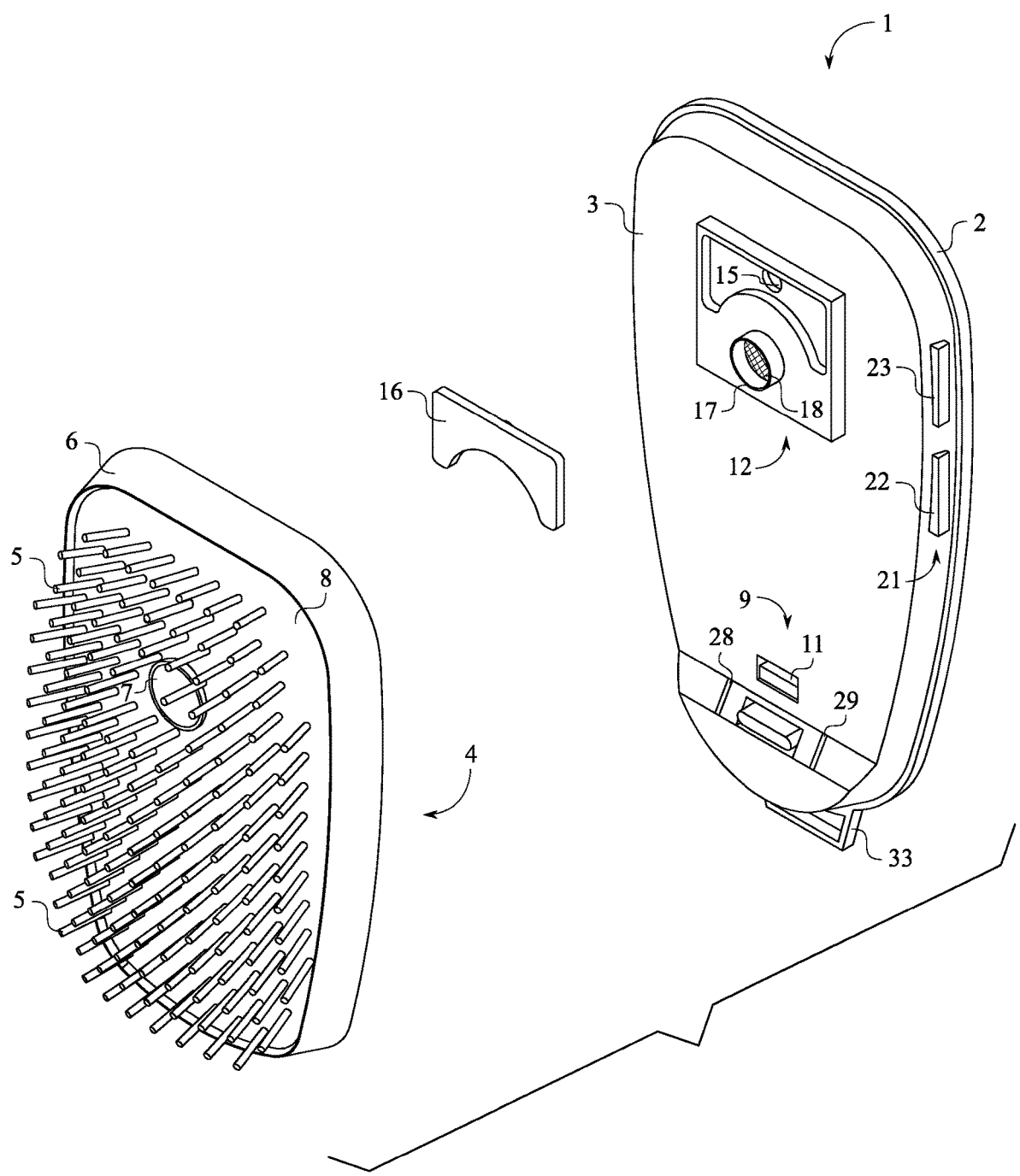
FIG. 3 is a top exploded perspective view showing the detachable panel separate from the handheld grip, wherein the inlet cover is shown detached from the reservoir inlet.
Figure 4:
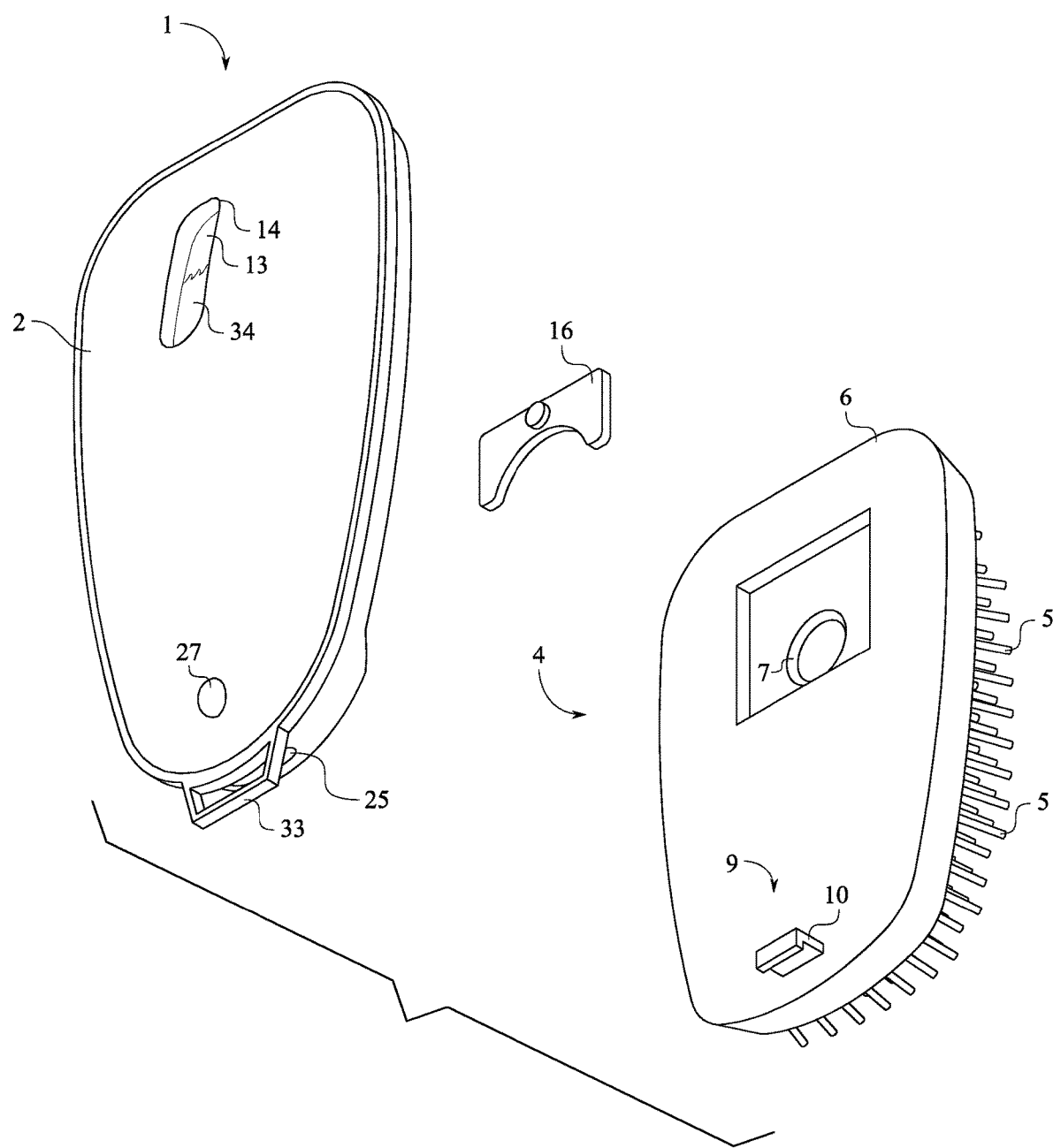
FIG. 4 is a bottom exploded perspective view showing the detachable panel separate from the handheld grip, wherein the inlet cover is shown detached from the reservoir inlet.
Figure 5:
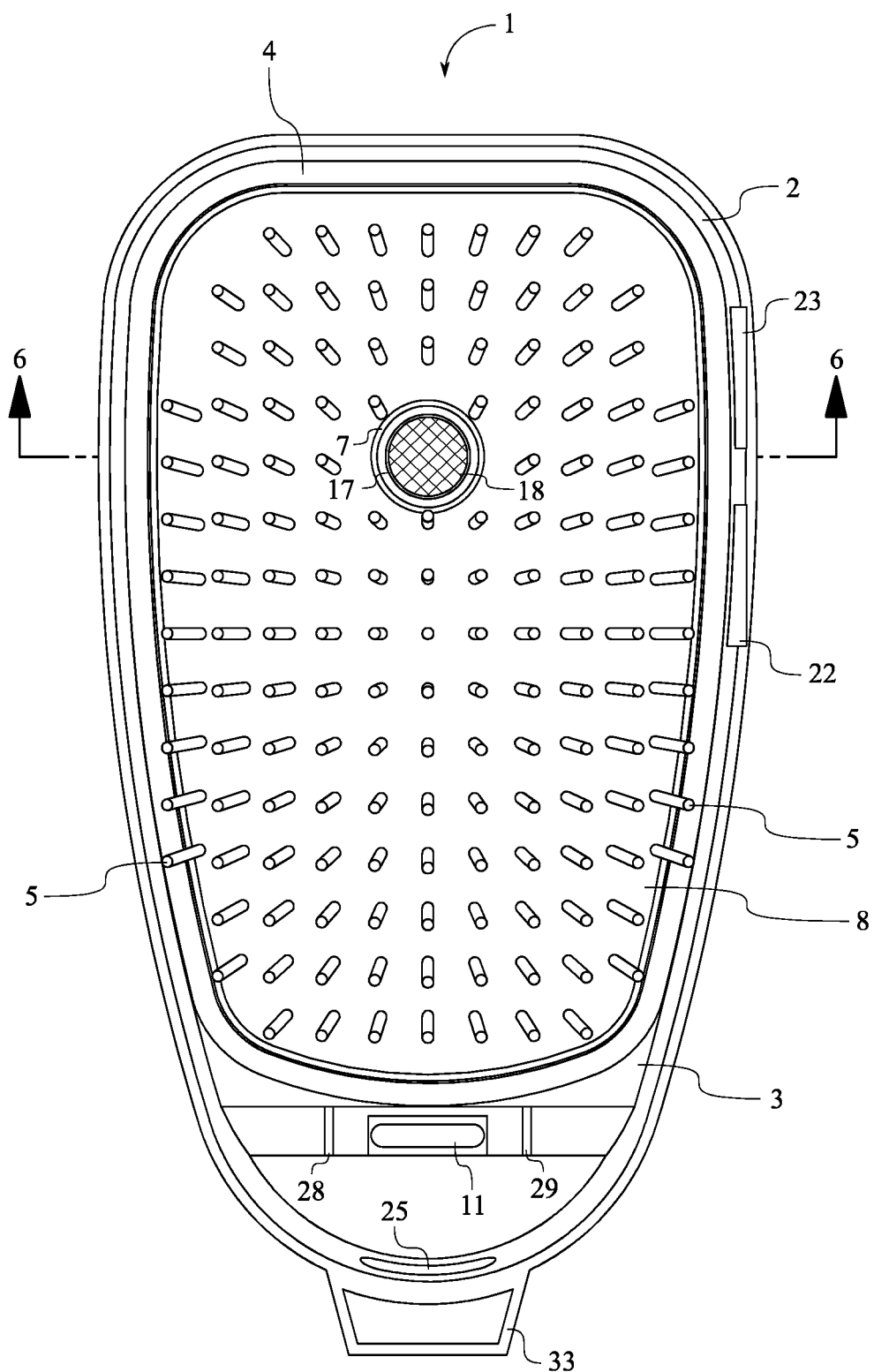
FIG. 5 is a front elevated view thereof showing the conditioning and styling reactivated hair device.
Figure 6:
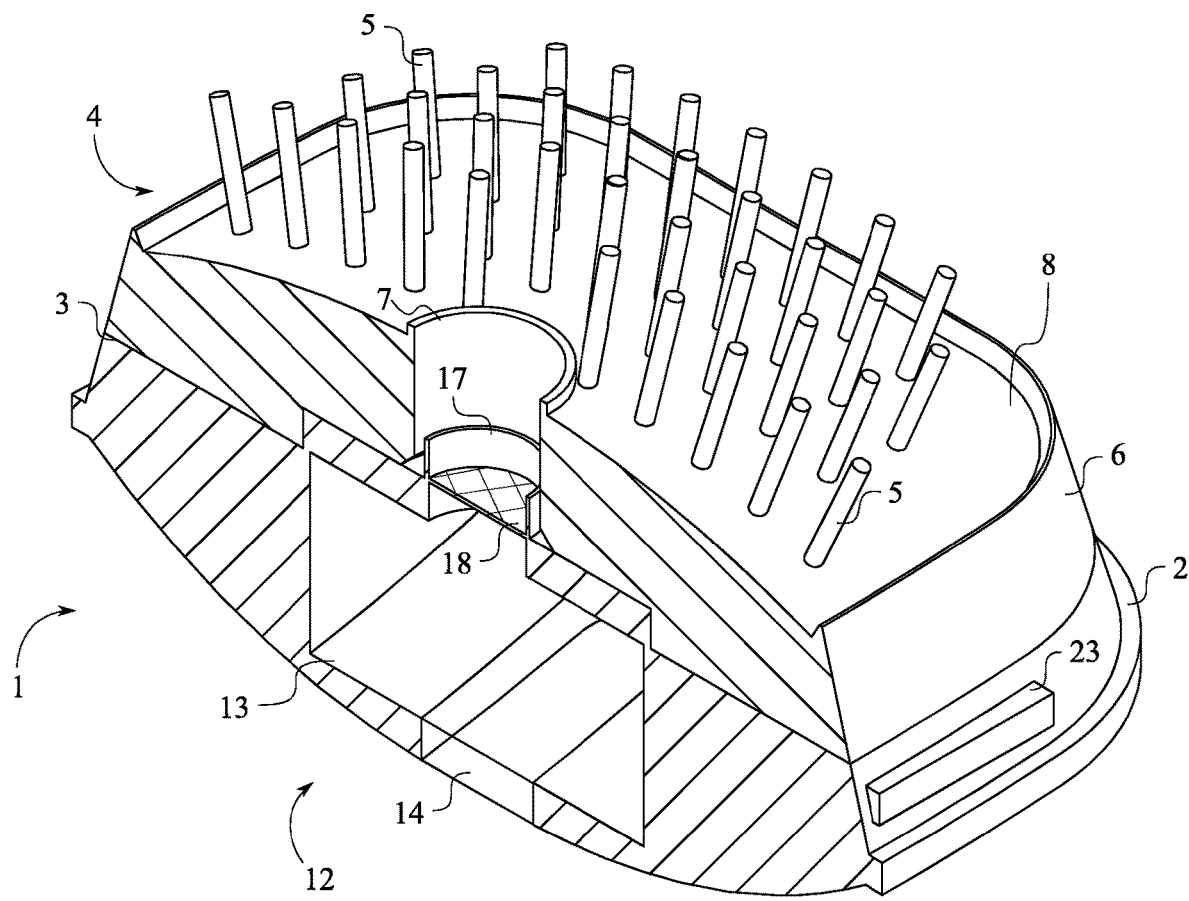
FIG. 6 is a cross-sectional view of the conditioning and styling reactivated hair device taken along line 6-6 of FIG. 5, wherein the outlet nozzle is shown in fluid communication with the flow guide.

The general configuration of the aforementioned components enables the present invention to dispense spray formulations 34 onto the hair for styling or conditioning purposes. As can be seen in FIGS. 3 and 4, the handheld grip 1 comprises a palm-bracing surface 2 and an interfacing surface 3. The detachable panel 4 a back plate 6 and a flow guide 7. The palm-bracing surface 2 and the interfacing surface 3 are positioned opposite to each other about the handheld grip 1 so the handheld grip 1 can be ergonomically held on the palm-bracing surface 2 by the one hand. The back plate 6 is attached onto and across the interfacing surface 3, so the detachable panel 4 covers the internal structure of the handheld grip 1. As can be seen in FIG. 7, The vibration mechanism 30 is operatively integrated into the handheld grip 1, wherein the vibration mechanism 30 is used to generate physical vibrations from the handheld grip 1. The physical vibrations generated by the vibration mechanism 30 are used to provide scalp stimulation. Similarly, the nebulizing mechanism 12 is operatively integrated into the handheld grip 1, wherein the nebulizing mechanism 12 is used to dispense spray formulations 34 from the handheld grip 1. The vibration mechanism 30 works in conjunction with the nebulizing mechanism 12 to dispense spray formulations 34 as an ultra-sonic mist. As can be seen in FIGS. 5 and 6, the flow guide 7 traverses through the back plate 6, and the nebulizing mechanism 12 is in fluid communication with the flow guide 7. Thus, the spray formulations 34 are dispensed in a predetermined orientation from the handheld grip 1. Further, to control the operation of the nebulizing mechanism 12 and the vibration mechanism 30, the control system 19 is electronically connected to the nebulizing mechanism 12 and the vibration mechanism 30.

Figure 8:
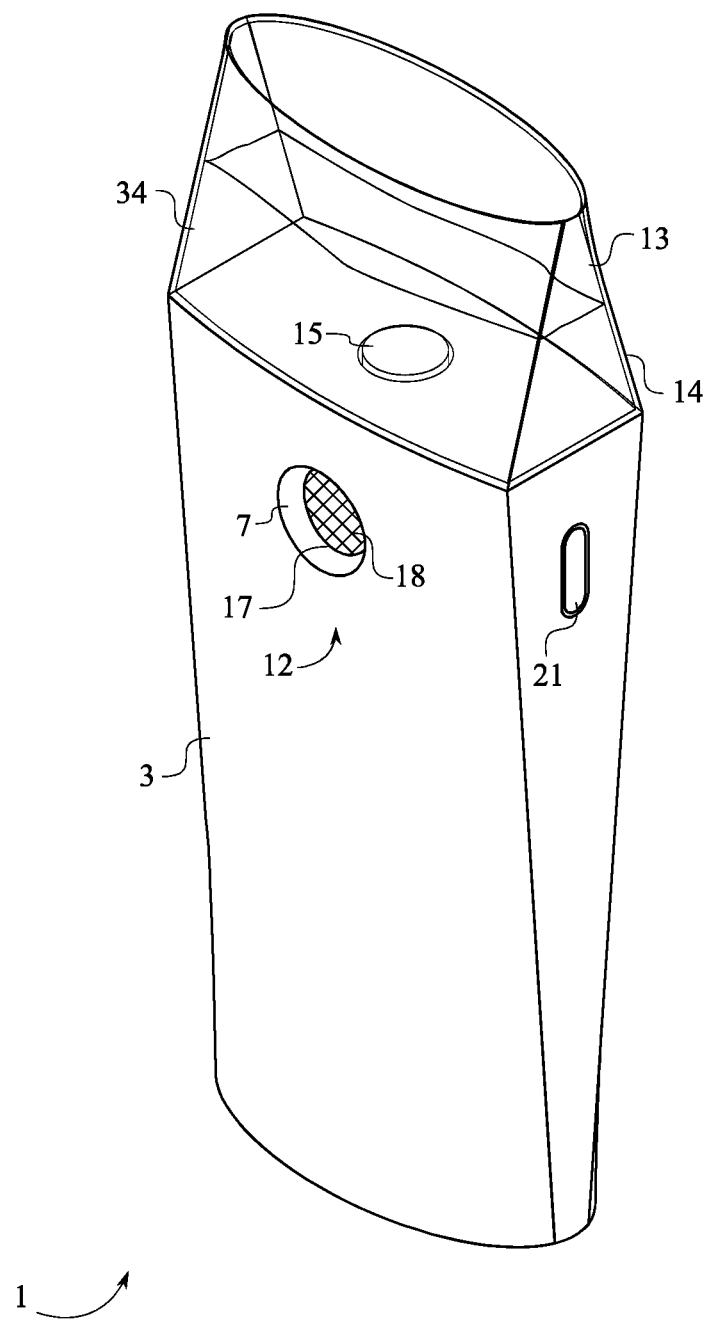
FIG. 8 is a top front perspective view showing an embodiment of the handheld grip, wherein the detachable panel is not included.
Figure 9:
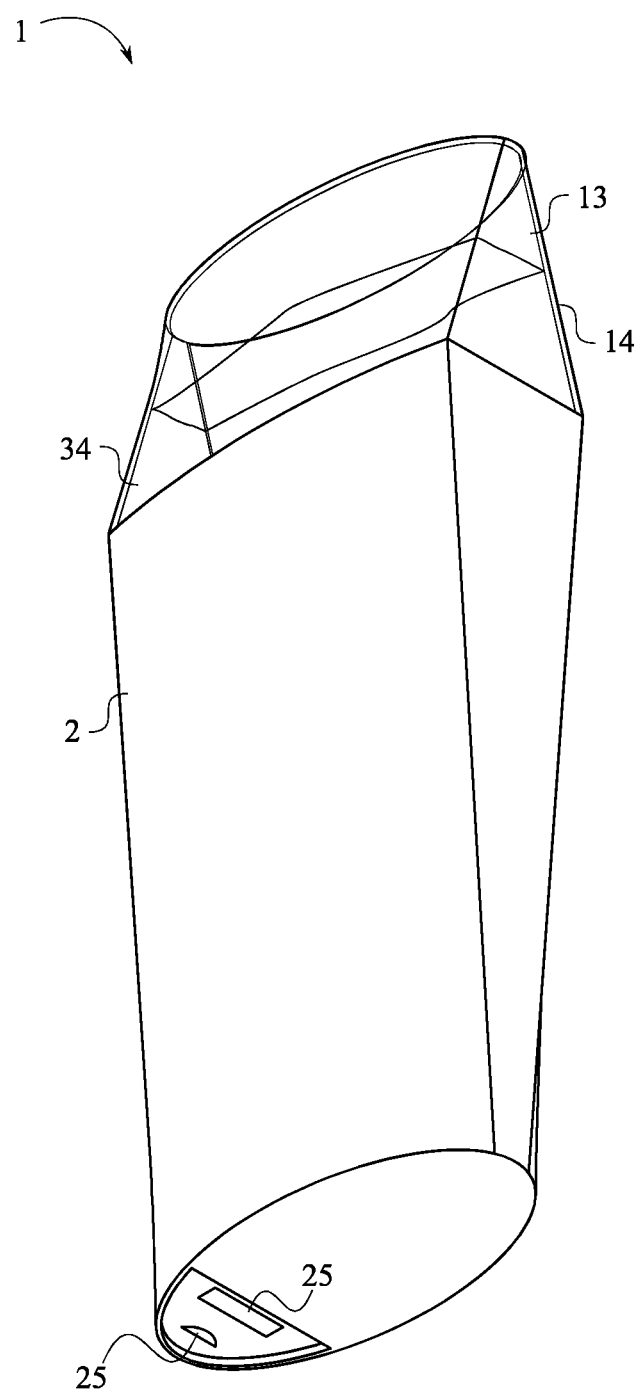
FIG. 9 is a bottom rear perspective view showing an embodiment of the handheld grip, wherein the detachable panel is not included.
Figure 11:
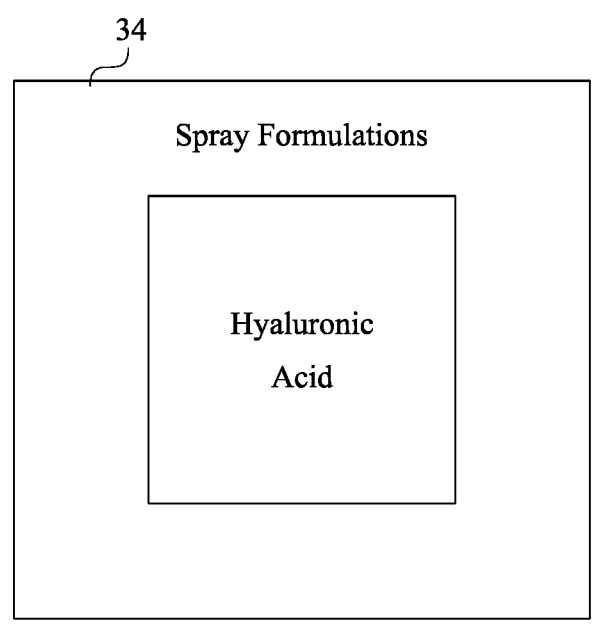

The spray formulations 34 dispensed by the nebulizing mechanism 12 hydrate the hair without damping the hair or leaving the hair sticky. As can be seen in FIG. 11, a quantity of Hyaluronic acid is an active ingredient of the spray formulations 34. Hyaluronic acid is a substance naturally present in the human body which is commonly used to treat skin wounds as well as a moisturizer. Further, the spray formulations 34 are preferably dispensed as an ultra-sonic mist, so the spray formulations 34 penetrate the hair to a deeper level. To accommodate the spray formulations 34, the nebulizing mechanism 12 is designed to fit the viscosity and texture of the spray formulations 34 and prevent damage or discoloration to the nebulizing mechanism 12. As can be seen in FIGS. 5 and 6, the nebulizing mechanism 12 comprises a reservoir 13, an outlet nozzle 17, and a nebulizer 18. The reservoir 13 provides a storage space to store the spray formulations 34. The reservoir 13 is integrated within the handheld grip 1 to readily store the spray formulations 34 for selective dispensing of the spray formulations 34. As can be seen in FIGS. 5 and 6, the reservoir 13 is in fluid communication with the outlet nozzle 17 through the nebulizer 18, wherein the nebulizer 18 transforms the liquid state spray formulations 34 from the reservoir 13 to mist state spray formulations 34. The outlet nozzle 17 is also integrated into the interfacing surface 3 and is outwardly oriented from the interfacing surface 3 in order to direct the spray formulations 34 in the mist state away from the handheld grip 1. In addition, the outlet nozzle 17 is in fluid communication with the flow guide 7, so the spray formulations 34 in the mist state is guided through the detachable panel 4. In alternate embodiments, the reservoir 13 is provided as a detachable unit. As can be seen in FIGS. 8 and 9, the reservoir 13 can be attached to the handheld grip 1.

Furthermore, the reservoir 13 provides means for the users to monitor the levels of spray formulations 34 stored within the reservoir 13 as well as means to refill the reservoir 13 when necessary. As can be seen in FIG. 2, the reservoir 13 comprises a reservoir window 14, a reservoir inlet 15, and an inlet cover 16. The reservoir window 14 is integrated into the palm-bracing surface 2 to enable users to visually monitor the levels of spray formulations 34 within the reservoir 13. As can be seen in FIG. 3, the reservoir inlet 15 is integrated into the interfacing surface 3 in order to enable users to refill the reservoir 13 without obstructing the reservoir window 14. The inlet cover 16 is hingedly connected to the interfacing surface 3 and is positioned adjacent to the reservoir inlet 15 in order to enable the users to selectively open the reservoir inlet 15 to refill the reservoir 13. In a preferred embodiment, the reservoir 13, the reservoir window 14, the reservoir inlet 15, and the inlet cover 16 are made from specific materials resistant to rust or wear caused by the spray formulations 34. In alternate embodiments, the reservoir window 14 covers the entire body of the reservoir 13, as can be seen in FIGS. 8 and 9.

Figure 10:
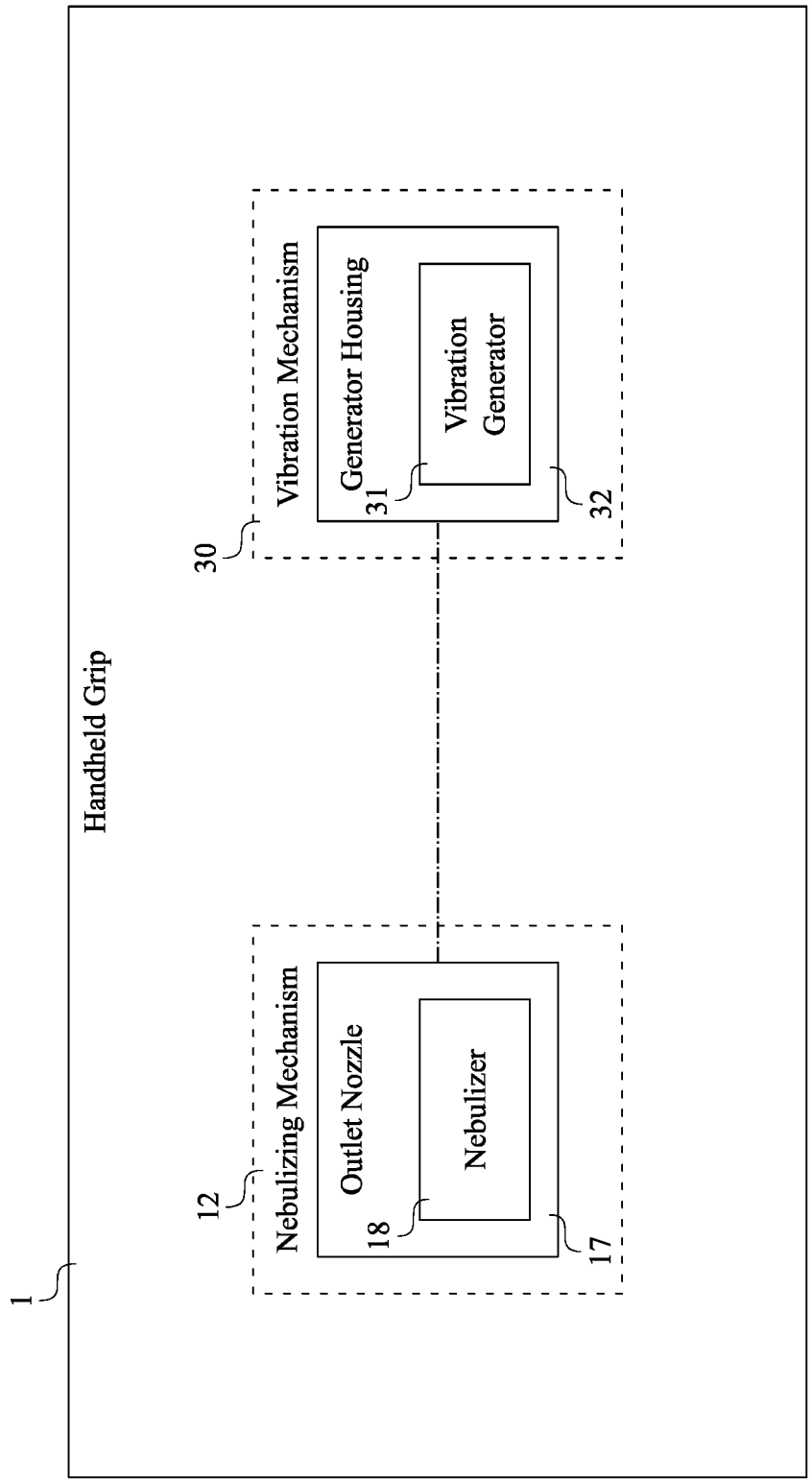
FIG. 10 is a schematic view of the nebulizing mechanism and the vibration mechanism showing the generator housing being in vibrational communication with the outlet nozzle.

To dispense the spray formulations 34 from the reservoir 13 in an ultra-sonic mist state, the vibration mechanism 30 is in vibrational communication with the outlet nozzle 17 of the nebulizing mechanism 12, as can be seen in FIG. 10. The nebulizer 18 is preferably a micro metal net which breaks down the size of the particles of the spray formulations 34 into much smaller particles, thus creating the ultra-sonic mist without the use of heat. As can be seen in FIG. 10, the vibration mechanism 30 comprises a vibration generator 31 and a generator housing 32. The vibration generator 31 is mounted within the generator housing 32 which is internally connected to the handheld grip 1. Thus, the ultra-sonic vibration from the vibration generator 31 is physically transmitted through the generator housing 32 to the nebulizer 18 to pump the spray formulations 34 though the micro metal net. In addition, the physical vibrations generated by the vibration generator 31 are physically transmitted through the generator housing 32 to the detachable panel 4 to provide physical stimulation to the scalp by positioning the detachable panel 4 against the scalp. To power up and control the nebulizing mechanism 12 and the vibration mechanism 30, the control system 19 is provided.

The control system 19 provides means for the user to operate the present invention with one hand. As can be seen in FIG. 7, the control system 19 comprises a controller 20, a plurality of controls 21, a power storage 24, a charger port 25, and a plurality of indicators 26. The power storage 24 is positioned within the handheld grip 1 to store energy which is used to power up the control system 19. The charger port 25 is peripherally connected onto the palm-bracing surface 2 to receive a power cord. The charger port 25 is also electrically connected to the power storage 24 to transmit power from an external power source through the power cord, through the charger port 25, and to the power storage 24. The power storage 24 is further electrically connected to the controller 20 to power up the controller 20. In some embodiments, the power storage 24 is a Lithium Ion battery and the power cord is a Universal Serial Bus (USB) cable. The controller 20 is also positioned within the handheld grip 1. The controller 20 is also electronically connected to the nebulizer 18 of the nebulizing mechanism 12, the vibration generator 31 of the vibration mechanism 30, the plurality of indicators 26, and the plurality of controls 21. The plurality of controls 21 is peripherally connected onto the palm-bracing surface 2 to receive manual commands from one hand of the user without requiring the use of another hand. Thus, the controller 20 receives electrical signals from the plurality of controls 21 corresponding to the manual commands of the user to selectively activate the nebulizer 18 and/or the vibration generator 31. In some embodiments, the controller 20 comprises pre-determined timers which shut-off the nebulizer 18 or vibration generator 31 after a certain time. The controller 20 also selectively activate the plurality of indicators 26 corresponding to the activated mechanism. The plurality of indicators 26 is connected onto the handheld grip 1 to indicate the mechanism being activated by the controller 20.

In some embodiments, the present invention provides individual controls and indicators corresponding to specific functions of the control system 19. As can be seen in FIG. 1, the plurality of controls 21 further comprises a vibration control 22 and a nebulizer control 23. The vibration control 22 is positioned adjacent to the flow guide 7 to enable the user to manually activate the vibration generator 31 of the vibration mechanism 30. Likewise, the nebulizer control 23 is positioned adjacent to the flow guide 7 to enable the users to manually activate the nebulizer 18 of the nebulizing mechanism 12. Like the plurality of controls 21, the plurality of indicators 26 provides individual visual indicators corresponding to specific functions. As can be seen in FIGS. 3 and 4, the plurality of indicators 26 comprises a power indicator 27, a vibration indicator 28, and a nebulizer indicator 29. The power indicator 27 is positioned on the palm-bracing surface 2, adjacent to the charger port 25, to indicate when the power storage 24 is being recharged. The vibration indicator 28 is positioned on the interfacing surface 3, adjacent to the charger port 25, to indicate when the vibration generator 31 is active. Finally, the nebulizer indicator 29 is positioned on the interfacing surface 3, adjacent to the charger port 25, to indicate when the nebulizer 18 is active. The vibration indicator 28 and the nebulizer indicator 29 are also oppositely positioned of each other about the charger port 25 to enable users to clearly determine the operation of the present invention. In alternate embodiments, the plurality of controls 21 comprises a single control which selectively activates the operation of the nebulizing mechanism 12, as can be seen in FIGS. 8 and 9.

In some embodiments, the present invention provides styling elements on the detachable panel 4 to help style the hair. As can be seen in FIG. 1, the detachable panel 4 further comprises a cushioning 8 and a plurality of bristles 5. The cushioning 8 is connected onto and across the back plate 6, opposite to the interfacing surface 3, to provide comfort while combing the hair. As can be seen in FIGS. 5 and 6, the plurality of bristles 5 is mounted across the cushioning 8, opposite to the back plate 6, to help style the hair. In addition, the plurality of bristles 5 transmits the physical vibrations from the vibration mechanism 30 to stimulate the scalp and help detangle hair while pressing the plurality of bristles 5 against the head of the user. Further, the present invention provides means to easily detach the detachable panel 4 from the handheld grip 1 to clean the plurality of bristles 5 and cushioning 8 on the detachable panel 4. The present invention further comprises a release mechanism 9. As can be seen in FIGS. 3 and 4, the release mechanism 9 is a mechanism which enables the quick detachment of the detachable panel 4 from the interfacing surface 3. The release mechanism 9 comprises a latch 10 and a spring lock 11. The latch 10 is integrated into the back plate 6, opposite to the plurality of bristles 5 of the detachable panel 4, which engages with the spring lock 11. The spring lock 11 is integrated into the interfacing surface 3, opposite the flow guide 7, to receive the latch 10 and to lock the detachable panel 4 onto the interfacing surface 3. Thus, the user can remove the detachable panel 4 from the interfacing surface 3 by unlocking the spring lock 11 to release the latch 10 and attach the detachable panel 4 to the interfacing surface 3 by engaging the latch 10 with the spring lock 11.

Furthermore, the present invention provides a means to hang the handheld grip 1 from an external object. As can be seen in FIGS. 1 and 2, the present invention further comprises an eyelet 33. The eyelet 33 is peripherally connected to the handheld grip 1, opposite to the flow guide 7, so the handheld grip 1 hangs from an external object.

Although the invention has been explained in relation to its preferred embodiment, it is to be understood that many other possible modifications and variations can be made without departing from the spirit and scope of the invention as hereinafter claimed.

What is claimed is:

1. A conditioning and styling reactivated hair device comprising:
   a handheld grip;
   a detachable panel;
   a nebulizing mechanism;
   a vibration mechanism;
   a control system;
   the handheld grip comprising a palm-bracing surface and an interfacing surface;
   the detachable panel comprising a back plate and a flow guide;
   the vibration mechanism comprising a vibration generator and a generator housing;
   the palm-bracing surface and the interfacing surface being positioned opposite to each other about the handheld grip;
   the vibration mechanism being operatively integrated into the handheld grip, wherein the vibration mechanism is used to generate physical vibrations from the handheld grip;
   the nebulizing mechanism being operatively integrated into the handheld grip, wherein the nebulizing mechanism is used to dispense spray formulations from the handheld grip;
   the back plate being attached onto and across the interfacing surface;
   the flow guide traversing through the back plate;
   the nebulizing mechanism being in fluid communication with the flow guide;
   the control system being electronically connected to the nebulizing mechanism and the vibration mechanism;
   the vibration generator being mounted within the generator housing; and,
   the generator housing being internally connected to the handheld grip.

2. The conditioning and styling reactivated hair device as claimed in claim 1, wherein a quantity of Hyaluronic acid is an active ingredient of the spray formulations.

3. The conditioning and styling reactivated hair device as claimed in claim 1 further comprising:
   the nebulizing mechanism comprising a reservoir, an outlet nozzle, and a nebulizer;
   the reservoir being integrated within the handheld grip;
   the reservoir being in fluid communication with the outlet nozzle through the nebulizer, wherein the nebulizer is used to transform the spray formulations within the reservoir from a liquid state to a mist state;
   the outlet nozzle being integrated into the interfacing surface;
   the outlet nozzle being outwardly oriented from the interfacing surface; and,
   the outlet nozzle being in fluid communication with the flow guide.

4. The conditioning and styling reactivated hair device as claimed in claim 3 further comprising:
   the reservoir comprising a reservoir window, a reservoir inlet, and an inlet cover;
   the reservoir window being integrated into the palm-bracing surface;
   the reservoir inlet being integrated into the interfacing surface;
   the inlet cover being hingedly connected to the interfacing surface; and,
   the inlet cover being positioned adjacent to the reservoir inlet.

5. The conditioning and styling reactivated hair device as claimed in claim 1 further comprising:
   the vibration mechanism being in vibrational communication with an outlet nozzle of the nebulizing mechanism.

6. The conditioning and styling reactivated hair device as claimed in claim 1 further comprising:
   the control system comprising a controller, a plurality of controls, a power storage, a charger port, and a plurality of indicators;
   the controller being positioned within the handheld grip;
   the plurality of controls being peripherally connected onto the palm-bracing surface;
   the power storage being positioned within the handheld grip;

the charger port being peripherally connected onto the palm-bracing surface;
the plurality of indicators being connected onto the handheld grip;
the charger port being electrically connected to the power storage;
the power storage being electrically connected to the controller; and,
the controller being electronically connected to a nebulizer of the nebulizing mechanism, a vibration generator of the vibration mechanism, the plurality of indicators, and the plurality of controls.

7. The conditioning and styling reactivated hair device as claimed in claim 6 further comprising:
the plurality of controls further comprising a vibration control and a nebulizer control;
the vibration control being positioned adjacent to the flow guide; and,
the nebulizer control being positioned adjacent to the flow guide.

8. The conditioning and styling reactivated hair device as claimed in claim 6 further comprising:
the plurality of indicators comprising a power indicator, a vibration indicator, and a nebulizer indicator;
the power indicator being positioned on the palm-bracing surface;
the power indicator being positioned adjacent to the charger port;
the vibration indicator being positioned on the interfacing surface;
the vibration indicator being positioned adjacent to the charger port;
the nebulizer indicator being positioned on the interfacing surface;
the nebulizer indicator being positioned adjacent to the charger port; and,
the vibration indicator and the nebulizer indicator being oppositely positioned of each other about the charger port.

9. The conditioning and styling reactivated hair device as claimed in claim 1 further comprising:
the detachable panel further comprising a cushioning and a plurality of bristles;
the cushioning being connected onto and across the back plate, opposite to the interfacing surface; and,
the plurality of bristles being mounted across the cushioning, opposite to the back plate.

10. The conditioning and styling reactivated hair device as claimed in claim 1 further comprising:
a release mechanism;
the release mechanism comprising a latch and a spring lock;
the latch being integrated into the back plate, opposite to a plurality of bristles of the detachable panel; and,
the spring lock being integrated into the interfacing surface, opposite the flow guide.

11. The conditioning and styling reactivated hair device as claimed in claim 1 further comprising:
an eyelet; and,
the eyelet being peripherally connected to the handheld grip, opposite to the flow guide.

12. A conditioning and styling reactivated hair device comprising:
a handheld grip;
a detachable panel;
a nebulizing mechanism;
a vibration mechanism;
a control system;
a release mechanism;
the handheld grip comprising a palm-bracing surface and an interfacing surface;
the detachable panel comprising a back plate and a flow guide;
the release mechanism comprising a latch and a spring lock;
the palm-bracing surface and the interfacing surface being positioned opposite to each other about the handheld grip;
the vibration mechanism being operatively integrated into the handheld grip, wherein the vibration mechanism is used to generate physical vibrations from the handheld grip;
the nebulizing mechanism being operatively integrated into the handheld grip, wherein the nebulizing mechanism is used to dispense spray formulations from the handheld grip;
the back plate being attached onto and across the interfacing surface;
the flow guide traversing through the back plate;
the nebulizing mechanism being in fluid communication with the flow guide;
the control system being electronically connected to the nebulizing mechanism and the vibration mechanism;
the latch being integrated into the back plate, opposite to a plurality of bristles of the detachable panel; and,
the spring lock being integrated into the interfacing surface, opposite the flow guide.

13. The conditioning and styling reactivated hair device as claimed in claim 12, wherein a quantity of Hyaluronic acid is an active ingredient of the spray formulations.

14. The conditioning and styling reactivated hair device as claimed in claim 12 further comprising:
the nebulizing mechanism comprising a reservoir, an outlet nozzle, and a nebulizer;
the reservoir comprising a reservoir window, a reservoir inlet, and an inlet cover;
the reservoir being integrated within the handheld grip;
the reservoir being in fluid communication with the outlet nozzle through the nebulizer, wherein the nebulizer is used to transform the spray formulations within the reservoir from a liquid state to a mist state;
the outlet nozzle being integrated into the interfacing surface;
the outlet nozzle being outwardly oriented from the interfacing surface;
the outlet nozzle being in fluid communication with the flow guide;
the reservoir window being integrated into the palm-bracing surface;
the reservoir inlet being integrated into the interfacing surface;
the inlet cover being hingedly connected to the interfacing surface; and,
the inlet cover being positioned adjacent to the reservoir inlet.

15. The conditioning and styling reactivated hair device as claimed in claim 12 further comprising:
the vibration mechanism comprising a vibration generator and a generator housing;
the vibration mechanism being in vibrational communication with an outlet nozzle of the nebulizing mechanism;
the vibration generator being mounted within the generator housing; and, the generator housing being internally connected to the handheld grip.

16. The conditioning and styling reactivated hair device as claimed in claim 12 further comprising:
the control system comprising a controller, a plurality of controls, a power storage, a charger port, and a plurality of indicators;
the controller being positioned within the handheld grip;
the plurality of controls being peripherally connected onto the palm-bracing surface;
the power storage being positioned within the handheld grip;
the charger port being peripherally connected onto the palm-bracing surface;
the plurality of indicators being connected onto the handheld grip;
the charger port being electrically connected to the power storage;
the power storage being electrically connected to the controller; and,
the controller being electronically connected to a nebulizer of the nebulizing mechanism, a vibration generator of the vibration mechanism, the plurality of indicators, and the plurality of controls.

17. The conditioning and styling reactivated hair device as claimed in claim 16 further comprising:
the plurality of controls further comprising a vibration control and a nebulizer control;
the plurality of indicators comprising a power indicator, a vibration indicator, and a nebulizer indicator;
the vibration control being positioned adjacent to the flow guide;
the nebulizer control being positioned adjacent to the flow guide;
the power indicator being positioned on the palm-bracing surface;
the power indicator being positioned adjacent to the charger port;
the vibration indicator being positioned on the interfacing surface;
the vibration indicator being positioned adjacent to the charger port;
the nebulizer indicator being positioned on the interfacing surface;
the nebulizer indicator being positioned adjacent to the charger port; and,
the vibration indicator and the nebulizer indicator being oppositely positioned of each other about the charger port.

18. The conditioning and styling reactivated hair device as claimed in claim 12 further comprising:
the detachable panel further comprising a cushioning;
the cushioning being connected onto and across the back plate, opposite to the interfacing surface; and,
the plurality of bristles being mounted across the cushioning, opposite to the back plate.

19. The conditioning and styling reactivated hair device as claimed in claim 12 further comprising:
an eyelet; and,
the eyelet being peripherally connected to the handheld grip, opposite to the flow guide.

* * * * *